United States Patent [19]

Das

[11] Patent Number: 4,542,155
[45] Date of Patent: Sep. 17, 1985

[54] TETRAHYDROFURANYL SUBSTITUTED PROSTAGLANDIN ANALOGS

[75] Inventor: Jagabandhu Das, Plainsboro, N.J.

[73] Assignee: E. R. Squibb & Sons, Inc., Princeton, N.J.

[21] Appl. No.: 595,772

[22] Filed: Apr. 2, 1984

[51] Int. Cl.[4] ............................................. C07D 307/16
[52] U.S. Cl. .................................... 514/461; 549/499; 549/501; 514/449
[58] Field of Search ................ 424/285; 549/501, 499; 514/461, 449

[56] References Cited

U.S. PATENT DOCUMENTS

| | | | |
|---|---|---|---|
| 3,906,004 | 9/1975 | Perry | 568/444 X |
| 3,935,240 | 1/1976 | Mallion | 568/27 X |
| 3,953,435 | 4/1976 | Hayashi et al. | 568/27 X |
| 3,975,532 | 8/1976 | Miller | 424/274 |
| 4,048,198 | 9/1977 | Nedenskov et al. | 549/501 |
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,360,688 | 11/1982 | Floyd, Jr. | 549/501 X |

FOREIGN PATENT DOCUMENTS

| | | | |
|---|---|---|---|
| 0043292 | 8/1982 | European Pat. Off. | 424/285 |
| 2039909 | 8/1980 | United Kingdom | 424/285 |

OTHER PUBLICATIONS

C. Lin et al., "J. Am. Chem. Soc.", vol. 104, pp. 1621–1628 (1982).

Primary Examiner—Joseph L. Schofer
Assistant Examiner—Fred Teskin
Attorney, Agent, or Firm—Lawrence S. Levinson; Burton Rodney

[57] ABSTRACT

Tetrahydrofuranyl substituted prostaglandin analogs are provided having the structural formula

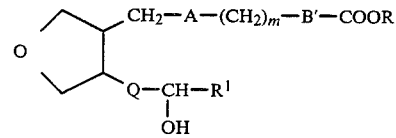

and including all stereoisomers thereof.

The compounds are cardiovascular agents useful, for example, in the treatment of thrombolytic disease.

17 Claims, No Drawings

TETRAHYDROFURANYL SUBSTITUTED PROSTAGLANDIN ANALOGS

DESCRIPTION OF THE INVENTION

The present invention relates to tetrahydrofuranyl substituted prostaglandin analogs which are cardiovascular agents useful, for example, in the treatment of thrombolytic disease. These compounds have the general formula

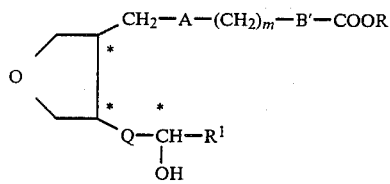

and including all stereoisomers thereof, wherein A is $-(CH_2)_2-$, $-CH=CH-$ or a single bond; m is 1 to 8; B' is a single bond or $-CH=CH-$ but where B' is $-CH=CH-$, m is 1 to 6; R is H, lower alkyl or alkali metal; Q is $-CH=CH-$ or $-(CH_2)_2-$; and $R^1$ is lower alkyl, aryl, aralkyl, cycloalkyl, cycloalkylalkyl or lower alkoxy.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent (for example,

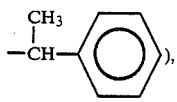

an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl or methylbenzyl

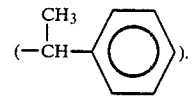

The term "cycloalkylalkyl" as used herein refers to cycloalkyl groups as defined above linked to an alkyl group as defined above.

The term "lower alkoxy", "alkoxy" or "aralkoxy" includes any of the above lower alkyl, alkyl or aralkyl groups linked to an oxygen atom.

The terms "halogen" or "halo" as used herein refers to chlorine, bromine, fluorine or iodine with chlorine being preferred.

The terms "$(CH_2)_m$" and "$(CH_2)_2$" includes straight or branched chain radicals having from 1 to 8 carbons in the normal chain in the case of $(CH_2)_m$ and 2 carbons in the normal chain in the case of $(CH_2)_2$, and may contain one or more lower alkyl substituents. Examples of $(CH_2)_m$ and $(CH_2)_2$ groups include

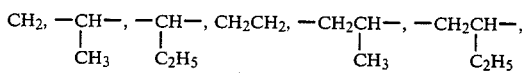

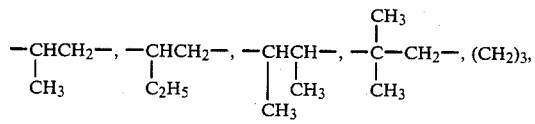

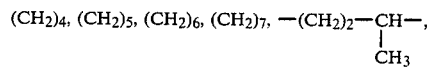

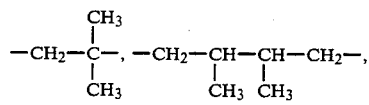

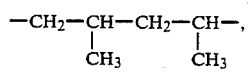

and the like.

Preferred are those compounds of formula I wherein A is $-CH=CH-$ or $-(CH_2)_2-$, B' is a single bond, m is 2 or 5, Q is $-CH=CH-$, R is hydrogen and $R^1$ is lower alkyl, phenyl, cycloalkyl or benzyl.

The various compounds of the invention may be prepared as outlined below.

The compounds of formula I of the invention are prepared from the aldehyde intermediate II

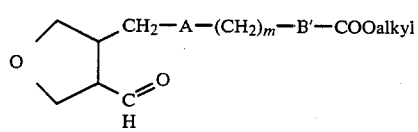

the preparation of which is described below.

The aldehyde intermediate II

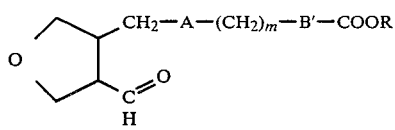

wherein A is —CH=CH may be prepared as follows.

1-Trimethylsilyloxy-1,3-butadiene A in an inert organic solvent such as methylene chloride, ether or tetrahydrofuran is made to react with maleic anhydride B in a Diels-Alder reaction to form the anhydride C

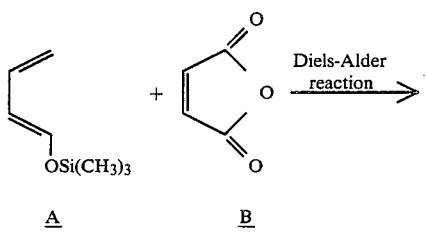

The anhydride C is reduced, for example, by treatment with a reducing agent such as lithium aluminum hydride, in the presence of an inert organic solvent such as tetrahydrofuran to form triol D

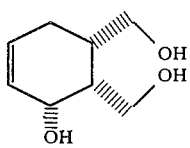

The triol D is then made to undergo acetonide formation by reacting D with p-toluene sulfonic acid in an inert organic solvent such as acetone, or with 2,2-dimethoxy propane or 2-methoxy propene in methylene chloride and under an inert atmosphere to form acetonide E

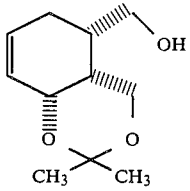

Acetonide E is then tosylated by reacting E in a solution of methylene chloride and weak organic base such as pyridine, with p-toluenesulfonyl chloride to form the tosylate F

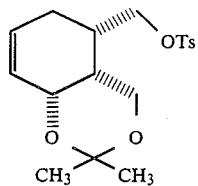

Tosylate F is then hydrolyzed by treatment with strong acid, such as HCl, oxalic acid or Amberlyst Resin/methanol in the presence of an inert organic solvent such as tetrahydrofuran to form alcohol G

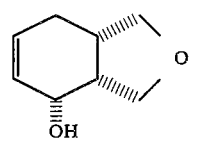

Next, the alcohol G is benzylated by reacting G with benzylbromide in the presence of sodium hydride and an inert organic solvent such as dimethylformamide to form benzylether H

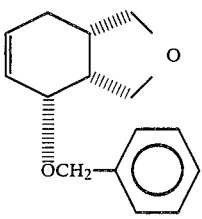

which is then made to undergo osmylation by reacting H with osmium tetroxide in the presence of N-methylmorpholine-N-oxide and appropriate inert organic solvent such as tetrahydrofuran to form diol J

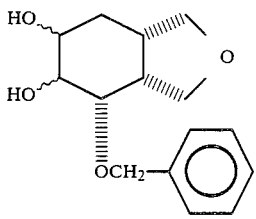

The diol J is next subjected to periodate cleavage by reacting it in an alcohol solvent such as methanol with sodium metaperiodate to form dialdehyde K

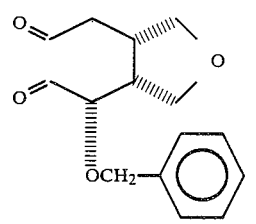

The dialdehyde K is then reduced by treatment with lithium aluminum hydride or other reducing agent such as sodium borohydride or lithium borohydride in the presence of an inert organic solvent such as methanol or tetrahydrofuran, to form the diol L

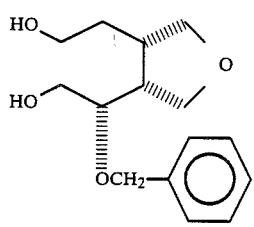

L which is then made to undergo hydrogenolysis by treatment of L with hydrogen in the presence of a palladium over carbon catalyst in ethyl acetate and glacial acetic acid, to form triol M

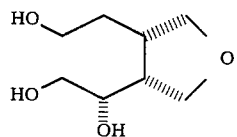

M

The triol M is next subjected to acetonide formation by reacting M with p-toluenesulfonic acid in the presence of an inert organic solvent such as acetone, to form the alcohol N

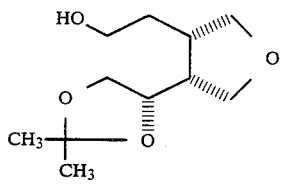

N which is oxidized by reacting with pyridinium chlorochromate in the presence of an inert organic solvent such as methylene choride, or with chromium trioxide in pyridine to form aldehyde O

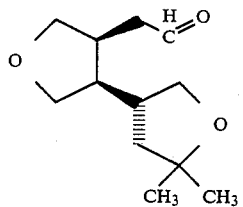

O

Aldehyde O is next subjected to a Wittig reaction wherein a mixture of triphenylphosphonium compound P

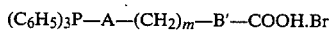

(C$_6$H$_5$)$_3$P—A—(CH$_2$)$_m$—B'—COOH.Br      P such as (4-carboxybutyl)-triphenylphosphonium bromide salt in tetrahydrofuran and potassium t-amylate in toluene is reacted with aldehyde O to form acid Q

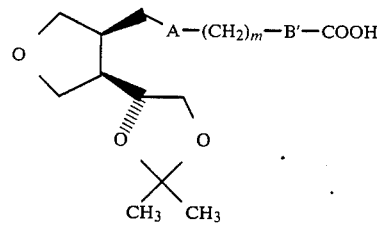

Q which is then dissolved in ether and reacted with diazomethane to form ester R

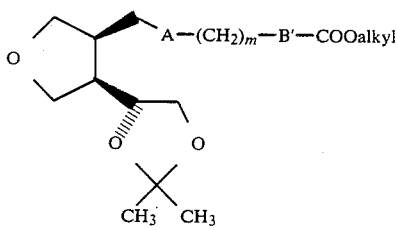

R

Ester R is then made to undergo acetal exchange by reacting R in methanol with p-toluene sulfonic acid to form diol S

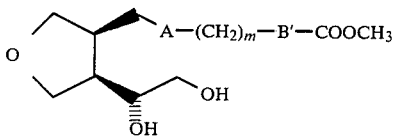

S which is then subjected to periodate cleavage by reacting S in methanol with sodium metaperiodate to form aldehyde IIA

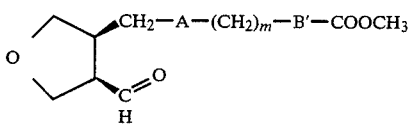

IIA

The intermediate aldehyde of formula II wherein A is —(CH$_2$)$_2$— are prepared by reducing compound S by treatment with hydrogen in the presence of palladium on charcoal to form compound S'

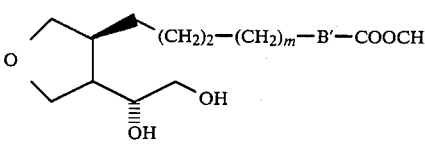

S' which is subjected to periodate cleavage as described above to form aldehyde IIAA

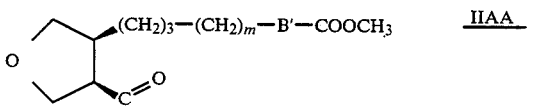

IIAA

The aldehyde II, IIA or IIAA may be employed as an intermediate in forming the cis series of compounds, that is

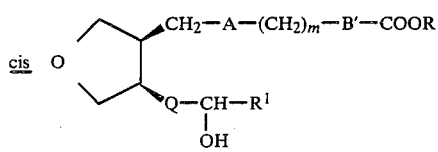   IA as opposed to the trans series whose preparation is described later

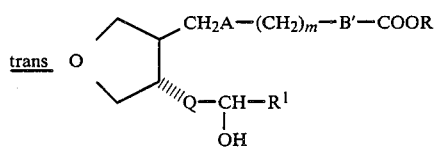   IB

In forming the cis series of the invention wherein Q is CH=CH, the aldehyde II, IIA or IIAA is subjected to a phosphonate reaction wherein the aldehyde is reacted with a phosphonate T

   T in the presence of sodium hydride and dimethoxyethane to form enone III

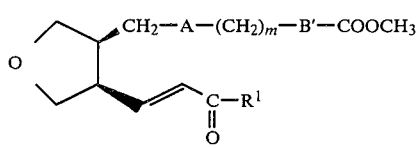   III which is reduced by treating III with a reducing agent such as sodium borohydride or zinc borohydride in the presence of cerium trichloride and methanol to form allylic alcohols IV and IVA

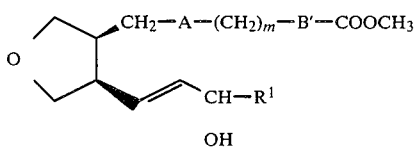   IV

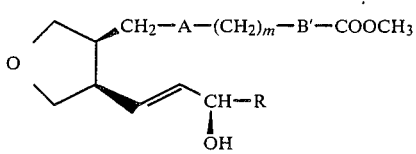   IVA

Allylic alcohol compounds IV and IVA may be separated on a silica gel column and the desired allylic alcohol may then be hydrolyzed by treatment with a strong base such as lithium hydroxide, potassium carbonate or sodium hydroxide to form the corresponding alkali metal salt which is treated with strong acid such as HCl to form the acid of the invention V or VA

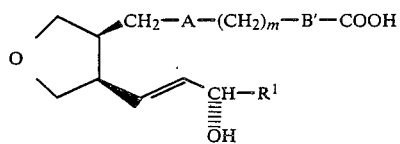   V

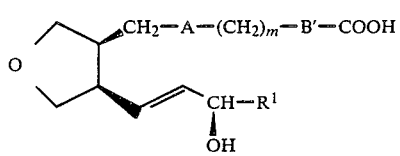   VA

The aldehyde II, IIA or IIAA may be employed as an intermediate in forming the trans series IB as follows. The aldehyde II, IIA or IIAA is subjected to an epimerization reaction wherein the aldehyde in methanol is reacted with sodium methoxide to form the aldehyde VI

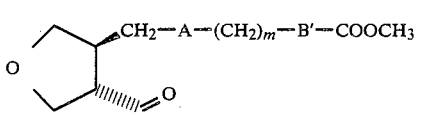   VI which is subjected to a phosphonate reaction as described above wherein VI is reacted with phosphonate T

   T in the presence of sodium hydride and dimethoxyethane to form enone VII

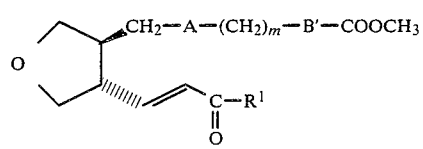   VII which is reduced by treating VII with a reducing agent such as sodium borohydride or zinc borohydride in the presence of cerium trichloride and methanol to form allylic alcohols VIII and VIIIA

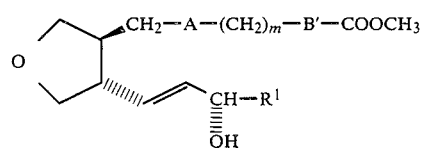   VIII

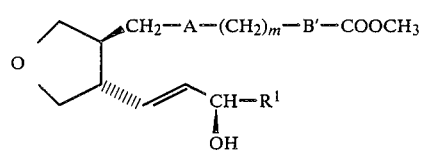   VIIIA

Allylic alcohols VIII and VIIIA may be separated on a silica gel column and the desired allylic alcohol may then be hydrolyzed by treatment with a strong base such as lithium hydroxide, potassium carbonate or sodium hydroxide to form the corresponding alkali metal salt which is treated with strong acid such as HCl to form the acid of the invention IX or IXA

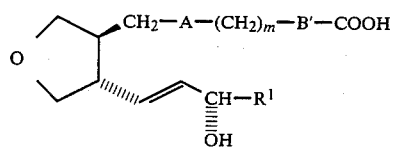  IX

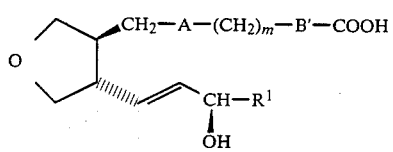  IXA

Compounds of formula I of the invention wherein B' is —CH=CH— and m is 1 to 6 may be prepared by subjecting any of the alcohols of the invention of the structure

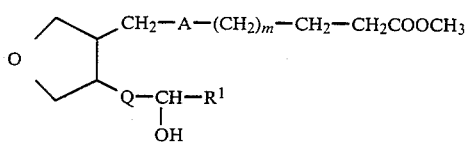  X wherein

Q is CH=CH or (CH$_2$)$_2$,

A is CH=CH, a single bond or (CH$_2$)$_2$, to tetrahydropyranyl ether formation by reacting alcohol X with dihydropyran in the presence of an inert organic solvent such as methylene chloride, chloroform and catalytic amounts of p-toluene sulfonic acid at reduced temperatures of from about 0° C. to about 10° C., to form the tetrahydropyranyl ether of formula XI

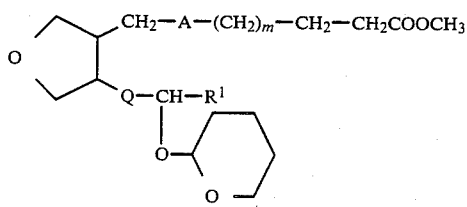  XI

The tetrahydropyranyl ether XI is then subjected to phenylselenylation by reacting XI with lithium diisopropyamide at reduced temperatures of from about −78° C. to less than about 0° C. in the presence of an inert organic solvent such as tetrahydrofuran, dimethoxy ethane or ether; thereafter a solution of diphenyldiselenide in an inert organic solvent as described above is added and the reaction is maintained at reduced temperatures as described above to form the selenophenyl ester XII

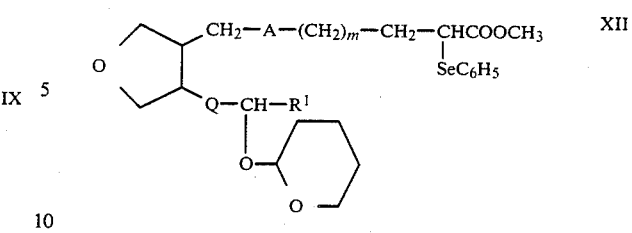  XII

The selenophenyl ester XII is hydrolyzed by treatment with a base such as lithium hydroxide, potassium carbonate or sodium hydroxide in the presence of an inert organic solvent such as tetrahydrofuran, methanol or dimethoxyethane-water and then with a strong acid such as HCl to form the acid XIII

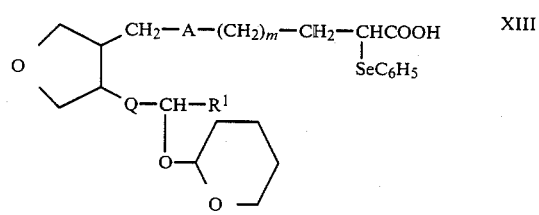  XIII

Acid XIII is then oxidized by reaction with hydrogen peroxide in the presence of an inert organic solvent such as tetrahydrofuran at reduced temperatures of from about 0° C. to about 25° C. to the α,β-unsaturated acid XIV

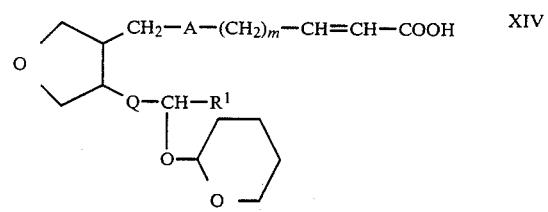  XIV which is then hydrolyzed by treatment with strong acid such as HCl in the presence of an inert organic solvent such as dimethoxyethane-water to form XV

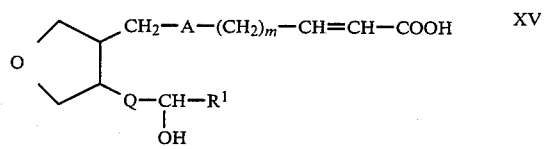  XV

Compounds of formula I wherein Q is —(CH$_2$)$_2$— may be prepared by subjecting any of the intermediates of the invention of the structure XVI

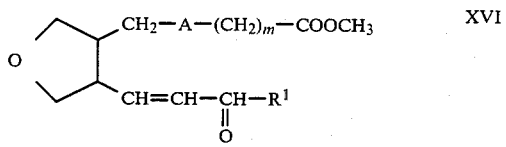  XVI to a reduction procedure wherein XVI is treated with a mixture of cuprous bromide and sodium bis(2-methoxyethoxy) aluminum hydride at a reduced temperature of from about −78° C. to about 0° C. to form XVII

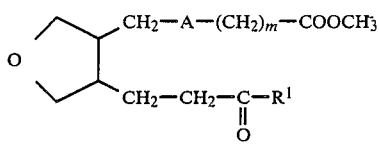   XVII which is then treated with cerium trichloride and sodium borohydride as described above with respect to conversion of III→IV and VII→VIII, to form

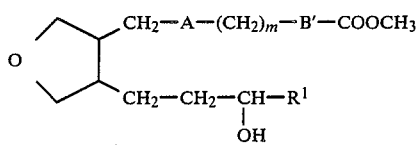   XVIII which may then be hydrolyzed to the corresponding acid XIX

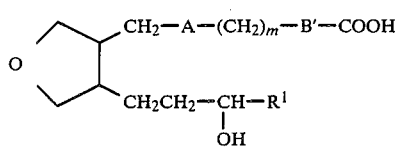   XIX

Compounds of formula I wherein Q is $-(CH_2)_2-$ may also be prepared by reducing any of the intermediates

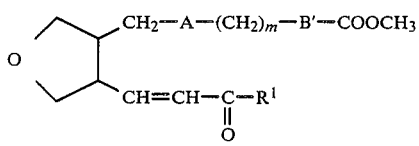   XVI by treatment with sodium borohydride in the presence of pyridine to form alcohol XVIII which may then be hydrolyzed to the corresponding acid XIX by treatment with alkali metal hydroxide and then HCl as described hereinbefore.

The compounds of this invention have three centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, all cis and all trans forms and stereoisomeric pairs may be prepared as shown in the working Examples which follow.

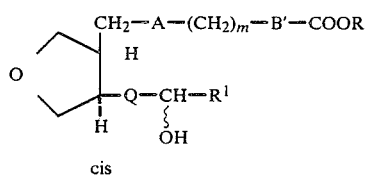   IA
cis

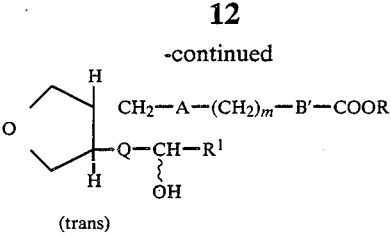   IB
(trans)

The wavy ( $\wr$ ) line in the above formulae indicates that the hydroxy group in each of the compounds of formulae IA–ID is either R(⊕) or S(α).

The compounds of this invention are cardiovascular agents useful in inhibiting arachidoninduced platelet aggregation, e.g., for treatment of thrombolytic disease, such as coronary or cerebral thromboses, and in inhibiting broncho-constriction as associated with asthma. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of the invention. Unless otherwise indicated, all temperatures are expressed in degrees Centigrade.

EXAMPLE 1

[3α(Z),4α(1E,3S)]-7-[Tetrahydro-4-(3-hydroxy-1-octenyl)-3-furanyl]-5-heptenoic acid, methyl ester A. (1α,2β,3β)-1-Trimethylsilyloxycyclohex-5-ene 2,3-dicarboxylic acid anhydride To a solution of 28.4 g of 1-trimethylsilyloxy-1,3-butadiene (0.2 mole) in 200 ml of $CH_2Cl_2$ at 25° C. was added 19.6 g of maleic anhydride (0.2 mole). The mixture was stirred at 25° C. for 24 hours then concentrated. The residue was purified on a LPS-1 silica gel column, eluting with 5% EtOAc/hexanes (3 liters) and 20% EtOAc/hexanes (4 liters) to give 26.0 g of title anhydride as a light yellow oil.

B. (1α,2β,3β)-1-Hydroxycyclohex-5-ene 2,3-dimethanol

To a suspension of 8.0 g of lithium aluminum hydride (210.5 mmole, 2 eq.) in 200 ml of dry THF at 0° C. was added slowly, a solution of 25 g of title A anhydride (104 mmole) in 150 ml of dry THF. The reaction was stirred at reflux for 4 hours and at 25° C. for 18 hours, then cooled to 0° C. and a saturated solution of $Na_2SO_4$ was added dropwise until no more white precipitates formed. It was then filtered. The white precipitates were washed thoroughly with THF, then stirred with 500 ml of 10% acetonitrile in ethylacetate for 30 minutes and filtered. The combined filtrate was concentrated to give a viscous oil which was purified on a LPS-1 silica gel column, eluting with 50% EtOAc/hexanes and 5% methanol/EtOAc to give 14.98 g of title triol as a clear oil.

C.
(1α,9β,10β)-1-Hydroxymethyl-6,6-dimethyl-3,4-dehydro-5,7-dioxa-octalin To a solution of 14.98 g of title B triol (95 mmole) in 150 ml of dry acetone was added 30 g of dried 4A molecular sieves and 1 g of p-toluenesulfonic acid (5 mmole, 5 mole %). After stirring at 25° C. under an argon atomsphere for 18 hours, the reaction mixture was neutralized with solid sodium bicarbonate and filtered. The filtrate was concentrated to give an oil which was purified on a LPS-1 silica gel column, eluting with 5% EtOAc/hexanes and 10% EtOAc/hexanes to give 15.58 g of the title acetonide.

D.
(1α,9β,10β)-1-p-Toluenesulfonyloxymethyl-6,6-dimethyl-3,4-dehydro-5,7-dioxa-octalin To a solution of 6 g of title C acetonide (30 mmole) in 40 ml of dry methylene chloride and 20 ml of pyridine (150 mmole, 5 eq.) was added 7.63 g of p-toluenesulfonylchloride (40 mmole, 1.3 eq.). After stirring at 25° C. for 24 hours, the reaction mixture was diluted with ether and washed with water, 1N hydrochloric acid and brine. The aqueous layer was back-extracted with ether. The combined organic layer was dried over anhydrous $MgSO_4$ and concentrated to give title tosylate in the form of an oil which was used directly in the next reaction.

E. (4α,8β,9β)-4-Hydroxy-1,3,4,7,8,9-hexahydro isobenzofuran

To a solution of crude title D tosylate (6.30 mmole) in 40 ml of dry THF and 10 ml of $H_2O$ was added 20 ml of a 1N aqueous HCl solution. After stirring for 6 hours at 25° C., the reaction was neutralized with solid $NaHCO_3$ and diluted with methylene chloride. The layers were separated. The aqueous layer was extracted with methylene chloride. The combined organic layer was dried over anhydrous $MgSO_4$ and concentrated to give an oil which was purified on an LPS-1 silica gel column, eluting with 5-10% EtOAc/hexanes to give 3.85 g of title alcohol.

F. (4α,8β,9β)-4-Benzyloxy-1,3,4,7,8,9-hexahydro isobenzofuran

To a slurry of 1.44 g of prewashed sodium hydride (50% dispersion in mineral oil, 27.0 mmole, 1.6 eq.) in 20 ml of dry DMF at 0° C. was added a solution of 3.85 g title E alcohol (27.0 mmole) in 10 ml DMF. The mixture was stirred at 25° C. for 15 minutes, cooled to 0° C. and then 4.3 g of benzylbromide (27.0 mmole, 1.0 eq.) was added. After stirring for 30 minutes at 25° C., the reaction mixture was poured into 300 ml of a saturated aqueous ammonium chloride solution and extracted with three 100 ml of water, dried over anhydrous $MgSO_4$ and concentrated. The residue was purified on an LPS-1 silica gel column, eluting with 10% EtOAc/hexanes to give 4.5 g of title benzylether as a yellow oil.

G. (4α,8β,9β)-4-Benzyloxy-5,6-dihydroxy octahydro-isobenzofuran

To 1.6 g of title F benzylether (6.95 mmole) in 70 ml of dry THF at 25° C. was added 1.17 g of N-methylmorpholine-N-oxide (8.34 mmole, 1.2 eq.) followed by dropwise addition of water until a homogeneous solution was obtained. To the resulting solution at 25° C. was added 353 μmole of a 5% solution of osmium tetroxide in ether (67.5 μmole, 1%). After stirring at 25° C. for 2 hours, 30 ml of a saturated aqueous sodium bisulfite solution was added to the mixture which was stirred at 25° C. for 30 minutes and extracted with three 100 ml portions of $CH_2Cl_2$. The combined organic layer was washed with 50 ml of 1N HCl solution, 50 ml of $H_2O$, dried over anhydrous $MgSO_4$ and concentrated to give 1.6 g title diol as a light brown solid. This was used without purification.

H.
[3α,4α(1S)]-2-[Tetrahydro-4-(1-benzyloxy-1-formylmethyl)-3-furanyl]acetaldehyde To 1.6 g title G diol (6.06 mmole) in 40 ml of methanol at 25° C. was added a solution of 1.48 g of sodium metaperiodate (6.0 mmole, 1.1 eq.) in 15 ml of water. After stirring at 25° C. for 1 hour, the reaction mixture was extracted with three 50 ml portions of $CH_2Cl_2$. The organic layer was dried over anhydrous $MgSO_4$ and concentrated to give 1.7 g title dialdehyde as a yellow oil. This was used without purification.

I.
[3α,4α(1S)]-2-[Tetrahydro-4-(1-benzyloxy-1-hydroxymethylmethyl)-3-furanyl]ethanol To a slurry of 460 mg of lithium aluminum anhydride (12.1 mmole, 4 eq.) in 50 ml of dry THF at 0° C. was added slowly a solution of 1.7 g crude title H dialdehyde (ca. 6.0 mmole) in 10 ml of dry THF. After stirring at 0° C. for 20 minutes, a saturated aqueous sodium sulfate solution was added dropwise until no more precipitates formed. The mixture was diluted with 300 ml of $CH_2Cl_2$ and stirred with anhydrous $MgSO_4$ for 30 minutes then filtered. The filtrate was concentrated to give 1.6 g title I diol as a clear oil.

J.
[3α,4α(1S)]-2-[Tetrahydro-4-(1-hydroxy-1-hydroxymethylmethyl)-3-furanyl]ethanol A mixture of 1.6 title I diol, 1.6 g of 10% palladium over carbon in 80 ml of EtOAc and 4 ml of glacial acetic acid was shaken in a Parr bottle under 50 lb. of hydrogen pressure at 25° C. for 24 hours. The mixture was then filtered through a bed of Celite. The filtrate was concentrated to give title J triol as a clear oil. This oil was used without purification.

K.
(3α,4α)-2-[Tetrahydro-4-(4,4-dimethyl-3,5-dioxacyclopentyl)-3-furanyl]ethanol To title J triol (ca. 6.0 mmole) in 20 ml of dry acetone was added 113 mg of p-toluenesulfonic acid (0.6 mmole, 10%) and 1.0 g of molecular sieves type 4 Å. After stirring at 25° C. for 4 hours, the reaction mixture was neutralized by addition of 80 mg solid sodium bicarbonate and filtered. The filtrate was concentrated to give a crude oil which was purified on a silica gel column, eluting with 50% EtOAc/hexanes (2 liters) and 3%

MeOH/CH$_2$Cl$_2$ (1 liter) to give 1.0 g of title K alcohol as a clear oil.

L.
(3α,4α)-2-[Tetrahydro-4-(4,4-dimethyl-3,5-dioxa-cyclopentyl)-3-furanyl]acetaldehyde To 300 mg of title K alcohol (1.4 mmole) in 10 ml of CH$_2$Cl$_2$ was added 1.0 g of Celite, followed by 595 mg of pyridinium chlorochromate (2.8 mmole, 2 eq.). After stirring for 2 hours at 25° C., the reaction mixture was diluted with 100 ml of ether and filtered through a bed of florosil. The filtrate was concentrated to give title L aldehyde as a clear oil. This was used directly in the next reaction.

M.
[3α(Z),4α]-7-[Tetrahydro-4-(4,4-dimethyl-3,5-dioxa-cyclopentyl)-3-furanyl]-5-heptenoic acid and

N.
[3α(Z),4α]-7-[Tetrahydro-4-(4,4-dimethyl-3,5-dioxa-cyclopentyl)-3-furanyl]-5-heptenoic acid, methyl ester To 927 mg of (4-carboxybutyl)-triphenylphosphonium bromide salt (2.1 mmole, 1.5 eq.) in 5 ml of dry THF at 0° C. was added dropwise 2.7 ml of a 1.43M solution of potassium t-amylate in toluene (3.9 mmole, 2.8 eq.). The mixture was stirred at 25° C. for 2 hours, cooled to 0° C. and a solution of title L aldehyde in 5 ml of THF (ca. 1.4 mmole) was added dropwise. After stirring at 25° C. for 1 hour, the reaction was quenched with glacial acetic acid and poured into 300 ml of brine and extracted with three 50 ml portions of EtOAc. The combined organic layer was concentrated. The residue was diluted with 50 ml of a saturated sodium bicarbonate solution, then extracted with three 50 ml portions of EtOAc. The aqueous layer was acidified to pH 5 with glacial acetic acid and extracted with four 50 ml portions of CH$_2$Cl$_2$. The organic layer was dried over anhydrous MgSO$_4$ and concentrated to give title M acid as a oil. This oil was dissolved in ether and methanol and treated with excess CH$_2$N$_2$ in ether to give 400 mg of a yellow oil after concentration. Purification was done on a silica gel column, eluting with 30% EtOAc/hexanes to give 210 mg of title N ester as a yellow oil.

O.
[3α(Z),4α(1S)]-7-[Tetrahydro-4-(1-hydroxy-1-hydroxymethylmethyl)-3-furanyl]-5-heptenoic acid, methyl ester To 180 mg of title N ester (0.57 mmole) in 2 ml of methanol was added 5.4 mg of p-toluene sulfonic acid (28.8 μm, 5%). The mixture was stirred at 25° C. for 4 hours, then concentrated. The residue was dissolved in 2 ml of fresh methanol and stirred at 25° C. for 18 hours, then concentrated. The residue was diluted with 30 ml of ether and filtered through a bed of silica gel. The filtrate was concentrated to give 127 mg of title diol as a clear oil.

P.
[3α(Z),4α]-7-[Tetrahydro-4-formyl-3-furanyl]-5-heptenoic acid, methyl ester To a solution of 127 mg of title O diol (0.40 mmole) in 5 ml of methanol at 25° C. was added a solution of 107 mg of sodium metaperiodate in 1 ml of H$_2$O. The mixture was stirred at 25° C. for 30 minutes, then extracted with three 10 ml portions of CH$_2$Cl$_2$. The organic layer was dried over anhydrous MgSO$_4$ and concentrated to give title aldehyde as a clear oil.

Q.
[3α(Z),4α(1E)]-7-[Tetrahydro-4-(3-oxo-1-octenyl)-3-furanyl]-5-heptenoic acid, methyl ester To a slurry of 24 mg of prewashed sodium hydride (50% dispersion in mineral oil, 0.5 mmole, 1 eq.) in 2 ml of dry dimethoxyethane (DME) at 0° C. was added 153 mg of 2-oxo-heptyldimethylphosphonate (0.69 mmole, 1.5 eq.). After stirring at 25° C. for 1 hour, the mixture was cooled to 0° C. and a solution of title p aldehyde in 2 ml of DME was added. The mixture was stirred at 25° C. for 3 hours, then quenched with glacial acetic acid and concentrated. The residue was diluted with 30 ml of ether and washed with 10 ml of saturated NaHCO$_3$, 10 ml of H$_2$O, dried over anhydrous MgSO$_4$ and concentrated to give 215 mg of crude title enone. This was used without purification.

R.
[3α(Z),4α(1E,3S)]-7-[Tetrahydro-4-(3-hydroxy-1-octenyl)-3-furanyl]-5-heptenoic acid, methyl ester To 215 mg of crude title Q enone (ca. 0.46 mm) in 2 ml of methanol at 25° C. was added 113 mg of cerium trichloride (0.46 mmole, 1 eq.). After stirring for 10 minutes at 25° C. the mixture was cooled to 0° C. and 17.5 mg of sodium borohydride (0.46 mmole, 4 eq.) was added. This mixture was stirred at 0° C. for 10 minutes, then poured into 100 ml of a saturated NH$_4$Cl solution, extracted with three 30 ml portions of ether, dried over anhydrous MgSO$_4$ and concentrated. Separation was done on a silica gel column, eluting with 20% EtOAc/hexanes to give 65 mg of the desired title allylic alcohol as a clear oil.

EXAMPLE 2
[3α(Z),4α(1E,3S)]-7-[Tetrahydro-4-(3-hydroxy-1-octenyl)-3-furanyl]-5-heptenoic acid, To 65 mg of Example 1 methyl ester (0.18 mmole) in 8 ml of THF and 2 ml of H$_2$O at 0° C. was added dropwise 1.8 ml of a 1M lithium hydroxide solution (1.8 mmole, 10 eq.). The mixture was stirred at 25° C. for 4 hours then concentrated. The residue was diluted with 5 ml of H$_2$O and acidified to pH 3 with a saturated oxalic acid solution, extracted with three 20 ml portions of ether, dried over anhydrous MgSO$_4$ and concentrated. The residue was purified on a CC-7 silica gel column, eluting with a gradient of pentane/ether. The product was kept under high vacuum for 7 days to give 47 mg of title acid as a clear oil.

TLC: silica gel; 5% MeOH/CH$_2$Cl$_2$; Rf~0.3.

Anal. Calcd for C$_{19}$H$_{32}$O$_4$, 0.17 H$_2$O: C, 69.69; H, 10.12; Found: C, 69.79; H, 9.97;

EXAMPLE 3
[3α(Z),4α(1E,3R)]-7-[Tetrahydro-4-(3-hydroxy-1-octenyl)-3-furanyl]-5-heptenoic acid, methyl ester The title methyl ester (also referred to in Example 1, Part R) was recovered from the mixture with the Example 1 methyl ester by chromatography on a silica gel column and elution with 20% ethylacetate in hexane. 35 Mg of title allylic alcohol was obtained.

EXAMPLE 4

[3α(Z),4α(1E,3R)]-[Tetrahydro-4-(3-hydroxy-1-octenyl)-3-furanyl]-5-heptenoic acid To 35 mg of Example 3 methyl ester (0.1 mmole) in 8 ml of THF and 2 ml of $H_2O$ at 0° C. was added dropwise 1.0 ml of a 1N lithium hydroxide solution (1.0 mmole, 10 eq.). The mixture was stirred at 25° C. for 4 hours then concentrated. The residue was diluted with 5 ml of $H_2O$, acidified to pH 3 with a saturated oxalic acid solution, extracted with three 20 ml portions of ether, dried over anhydrous $MgSO_4$ and concentrated. The residue was purified on a CC-7 silic gel column eluting with a gradient of pentane/ether. The product was kept under high vacuum for 2 days to give 25 mg of title acid as an oil.

TLC: Silica gel; 10% $MeOH/CH_2Cl_2$; $R_f \sim 0.4$

Anal. Calcd for $C_{19}H_{32}O_4$, 0.5 $H_2O$: C, 68.39; H, 9.97; Found: C, 68.39; H, 9.63.

EXAMPLE 5

[3α(Z),4α(1E,3S)]-7-[4-(3-Cyclohexyl-3-hydroxy-1-propenyl)tetrahydro-3-furanyl]-5-heptenoic acid, methyl ester

A.

[3α(Z),4α(1E)]-7-[4-(3-Cyclohexyl-3-oxo-1-propenyl)-tetrahydro-3-furanyl]-5-heptenoic acid, methyl ester To a slurry of 38.6 mg of prewashed sodium hydride (50% dispersion in mineral oil; 0.8 mmole, 1.1 eq.) in 5 ml of dry dimethoxyethane (DME) at 0° C. was added 222.3 mg of 2-oxo-2-cyclohexylethyldimethyl phosphonate (0.95 mmole, 1.3 eq.). After stirring at 25° C. for one hour, the mixture was cooled to °C. and a solution of 175.2 mg of Example 1, Part P aldehyde (0.73 mmole) in 5 ml of DME was added. The mixture was stirred at 25° C. for one hour then quenched with glacial acetic acid and concentrated. The residue was dilute with 30 ml of ether and washed with 10 ml of saturated $NaHCO_3$, 10 ml of $H_2O$, dried over anhydrous $MgSO_4$ and concentrated to give 300 mg crude title enone. This was used without purification.

B.

[3α(Z),4α(1E,3S)]-7-[4-(3-Cyclohexyl-3-hydroxy-1-propenyl)tetrahydro-3-furanyl]-5-heptenoic acid, methyl ester To 300 mg of crude title A enone (ca. 0.73 mmole) in 3 ml of methanol at 25° C. was added 172 mg of cerium trichloride (0.73 mmole, 1 eq.). After stirring at 25° C. for 10 minutes the mixture was cooled to 0° C. and 26.7 mg of sodium borohydride (0.73 mmole, 4 eq.) was added. The mixture was stirred at 0° C. for 10 minutes then poured into 100 ml of a saturated $NH_4Cl$ solution, extracted with three 30 ml portions of ether, dried over anhydrous $MgSO_4$ and concentrated. Separation was done on a silica gel column, eluting with 20% EtOAc/hexanes to give 104 mg of the desired title allylic alcohol as an oil.

EXAMPLE 6

[3α(Z),4α(1E,3S)]-7-[4-(3-Cyclohexyl-3-hydroxy-1-propenyl)tetrahydro-3-furanyl]-5-heptenoic acid To 104 mg of Example 5 methyl ester (0.29 mmole) in 8 ml of THF and 2 ml of $H_2O$ at 0° C. was added dropwise 2.9 ml of a 1M lithium hydroxide solution (2.9 mmole, 10 eq.). The mixture was stirred at 25° C. for 4 hours then concentrated. The residue was diluted with 5 ml of $H_2O$, acidified to portions of ether, dried over anhydrous $MgSO_4$ and concentrated. The residue was purified on a CC-7 silica gel column, eluting with a gradient of pentane/ether. The product was kept under high vacuum for 7 days to give 62 mg of title acid.

TLC: Silica gel; 10% $MeOH/CH_2Cl_2$; $R_f \sim 0.45$.

Anal Calcd for $C_{20}H_{32}O_4$, 0.33$H_2O$; C, 70.17; H, 9.62; Found: C, 70.17; H, 9.86.

EXAMPLE 7

[3α(Z),4α(1E,3S)]-7-[Tetrahydro-4-(3-hydroxy-4,4-dimethyl-1-octenyl)-3-furanyl]-5-heptenoic acid, methyl ester

A.

[3α(Z),4α(1E)]-7-[Tetrahydro-4-(3-oxo-4,4-dimethyl-1-octenyl)-3-furanyl]-5-heptenoic acid, methyl ester To a slurry of 43.2 mg of sodium hydride (0.9 mmole, 2.2 eq., 50% dispersion in mineral oil) in 10 ml of dry DME at 0° C. under an argon atmosphere was added 316 mg of 2-oxo-3,3-dimethyl heptyl dimethyl phosphonate (1.2 mmole, 3.0 eq.). The mixture was stirred for 1 hour at 25° C., cooled to 0° C. and a solution of 100 mg of Example 1, Part P aldehyde, (0.41 mmole) in 5 ml of dry DME was added. After stirring at 25° C. for 30 minutes, the reaction was quenched with glacial acetic acid and concentrated. The residue was diluted with 50 ml of ether and washed with two 10 ml portions of saturated $NaHCO_3$ and 10 ml of $H_2O$. The organic layer was dried over anhydrous $MgSO_4$ and concentrated to give crude title enone which was used directly in the next reaction.

B.

[3α(Z),4α(1E,3S)]-7-[Tetrahydro-4-(3-hydroxy-4,4-dimethyl-1-octenyl)-3-furanyl]-5-heptenoic acid, methyl ester and

C.

[3α(Z),4α(1E,3R)]-7-[Tetrahydro-4-(3-hydroxy-4,4-dimethyl-1-octenyl)-3-furanyl]-5-heptenoic acid, methyl ester To crude Part A enone (ca. 0.41 mmole) in 2 ml of dry methanol at 25° C. was added 100 mg of cerium trichloride (0.41 mmole, 1 eq.). The mixture was stirred at 25° C. for 10 minutes, cooled to 0° C. and 15.6 mg of sodium borohydride (0.41 mmole, 4 eq.) was added. After stirring at 0° C. for 10 minutes, the reaction mixture was poured into 50 ml of a saturated $NH_4Cl$ solution and extracted with three 20 ml portions of ether. The combined ethereal extract was dried over anhydrous $MgSO_4$ and concentrated.

Separation was done on silica gel column, eluting with 20% EtOAc/hexane to give 89 mg of title B ester and 23 mg of title C ester.

EXAMPLE 8

[3α(Z),4α(1E,3S)]-7-[Tetrahydro-4-(3-hydroxy-4,4-dimethyl-1-octenyl)-3-furanyl]-5-heptenoic acid To a solution of Example 7, Part B methyl ester (0.24 mmole) in 10 ml of THF at 25° C. was added 2.4 ml of a 1N lithium hydroxide solution (2.4 mmole, 10 eq.). The mixture was stirred at 25° C. for 3 hours and then concentrated.

The residue was diluted with 5 ml of $H_2O$, acidified to pH 3 with a saturated oxalic acid solution and extracted with three 20 ml portions of ether. The combined ethereal extract was washed with two 10 ml portions of H$_2$O, dried over anhydrous MgSO$_4$ and concentrated to give 87 mg of an oil.

Purification was done on a CC-7 silica gel column, eluting with a gradient of pentane/ether. The product collected was kept under high vacuum for 3 days to yield 47 mg of title acid.

TLC: silica gel; 5% MeOH/CH$_2$Cl$_2$; R$_f$= ~0.35.

Anal Calcd for C$_{21}$H$_{36}$O$_4$: C, 71.55, H, 10.29; Found: C, 71.34; H, 10.33.

EXAMPLE 9

[3α(Z),4α(1E,3R)]-7-[Tetrahydro-4-(3-hydroxy-4,4-dimethyl-1-octenyl)-3-furanyl]-5-heptenoic acid, methyl ester The title methyl ester was prepared as described in Example 7, Part C.

EXAMPLE 10

[3α(Z),4α(1E,3R)]-7-[Tetrahydro-4-(3-hydroxy-4,4-dimethyl-1-octenyl)-3-furanyl]-5-heptenoic acid To a solution of 23 mg of Example 9 methyl ester (0.06 mmole) in 2.4 ml of THF at 25° C. was added 0.6 ml of a 1N lithium hydroxide solution (0.6 mmol, 10 eq.). The mixture was stirred at 25° C. for 20 hours then concentrated. The residue was diluted with 5 ml of H$_2$O, acidified to pH 3 with a saturated oxalic acid solution and extracted with three 10 ml portions of ether. The combined ethereal extract was washed with two 10 ml portions of H$_2$O, dried over anhydrous MgSO$_4$ and kept under high vacuum for 2 days to yield 20 mg of title acid as an oil.

TLC: silica gel; 7% MeOH/CH$_2$Cl$_2$; R$_f$~0.45

Anal Calcd for C$_{21}$H$_{36}$O$_4$: C, 71.55; H, 10.29; Found: C, 71.14; H, 10.47.

EXAMPLE 11

[3α(Z),4α(1E,3S,4S)]-7-[Tetrahydro-4-(3-hydroxy-4-phenyl-1-pentenyl)-3-furanyl]-5-heptenoic acid, methyl ester

A.

[3α(Z),4α(1E,4S)]-7-[Tetrahydro-4-(3-oxo-4-phenyl-1-pentenyl)-3-furanyl]-5-heptenoic acid, methyl ester To a solution of 234.6 mg of (+)-2-oxo-4-methyl-4-phenylmethyl dimethyl phosphonate (0.9 mmole, 1.1 eq.) in 5 ml of dry THF at −78° C. under an argon atmosphere was added dropwise a solution of 371 μl of a 2.25M solution of n-butyl lithium in hexane (0.83 mm, 1.0 eq.). After stirring at −78° C. for 1 hour, the mixture was warmed to 25° C. and a solution of 200 mg of Example 1, Part P aldehyde (0.83 mmole) in 5 ml of dry THF was added. The reaction mixture was stirred at 25° C. for 1 hour then quenched with glacial acetic acid and concentrated. The residue was diluted with 50 ml of ether and washed with 20 ml of saturated NaHCO$_3$, 20 ml of H$_2$O, dried over anhydrous MgSO$_4$ and concentrated. Purification was done on a silica gel column, eluting with 20% EtOAc/hexane to give 230 mg of title enone.

B.

[3α(Z),4α(1E,3S,4S)]-7-[Tetrahydro-4-(3-hydroxy-4-phenyl-1-pentenyl)-3-furanyl]-5-heptenoic acid, methyl ester and

C.

[3α(Z),4α(1E,3R,4S)]-7-[Tetrahydro-4-(3-hydroxy-4-phenyl-1-pentenyl)-3-furanyl]-5-heptenoic acid, methyl ester To 230 mg of Part A enone (0.62 mmole) in 5 ml of methanol at 25° C. was added 151 mg of cerium trichloride (0.62 mmole, 1 eq.). After stirring at 25° C. for 10 minutes, the mixture was cooled to 0° C. and 23.6 mg of sodium borohydride was added (0.62 mmole, 4 eq.). The mixture was stirred at 0° C. for 10 minutes then poured into 50 ml of a saturated NH$_4$Cl solution and extracted with three 30 ml portions of ether. The combined ethereal extract was washed with two 20 ml portions of H$_2$O, dried over anhydrous MgSO$_4$ and concentrated.

Separation was done on a silica gel column, eluting with 50% EtOAc/hexane to give 38 mg of title B ester and 100 mg of title C ester.

TLC of title C ester:silica gel; EtOAc/hexane (2:1); R$_f$= ~0.6

TLC of title B ester:silica gel; EtOAC/hexane (2:1); R$_f$= ~0.5

EXAMPLE 12

[3α(Z),4α(1E,3S,4S)]-7-[Tetrahydro-4-(3-hydroxy-4-phenyl-1-pentenyl)-3-furanyl]-5-heptenoic acid To 38 mg of Example 11, Part B ester (0.1 mmole) in 4 ml of THF at 25° C. was added 1 ml of a 1M lithium hydroxide solution. The mixture was stirred at 25° C. for 20 hours and then concentrated. The residue was diluted with 5 ml of H$_2$O, acidified to pH 3 with a saturated oxalic acid solution and extracted with three 10 ml portions of ether. The combined ethereal extract was washed with two 10 ml portions of H$_2$O, dried over anhydrous MgSO$_4$ and concentrated. The product was kept under high vacuum for 2 days to yield 22.5 mg of title acid as an oil.

TLC: silica gel; 10% MeOH/CH$_2$Cl$_2$; R$_f$= ~0.45

Anal Calcd for C$_{22}$H$_{30}$O$_4$: C, 71.55; H, 10.29; Found: C, 71.14; H, 10.47.

EXAMPLE 13

[3α(Z),4β(1E,3S)]-7-[4-(3-Cyclohexyl-3-hydroxy-1-propenyl)tetrahydro-3-furanyl]-5-heptenoic acid, methyl ester

A.

[3α(Z),4β]-7-[Tetrahydro-4-formyl-3-furanyl]-5-heptenoic acid, methyl ester

To 140 mg of Example 1, Part P aldehyde (0.58 mmole) in 2 ml of methanol was added 3.15 mg of sodium methoxide (58 μmole, 10%). After stirring at 25° C. for 2 hours, the reaction mixture was poured into 50 ml of a saturated aqueous ammonium chloride solution and extracted with three 10 ml portions of ether. The organic layer was washed with 10 ml of H$_2$O and dried over anhydrous MgSO$_4$ and concentrated to give 130 mg of title aldehyde as an oil. This was used without purification.

B.

[3α(Z),4β(1E)]-7-[Tetrahydro-4-(3-oxo-3-cyclohexyl-1-propenyl)-3-furanyl]-5-heptenoic acid, methyl ester To a slurry of 28.6 mg of prewashed sodium hydride (50% dispersion in mineral oil, 0.6 mmole, 1.1 eq.) in 5 ml of dry dimethoxyethane (DME) at 0° C. was added 152 mg of 2-oxo-2-cyclohexylethyldimethylphosphonate (0.65 mmole, 1.2 eq.). After stirring at 25° C. for 1 hour, the mixture was cooled to 0° C. To this mixture was added a solution of 130 mg of title A aldehyde (0.54 mmole) in 5 ml of DME. The mixture was stirred at 25° C. for 30 minutes, then quenched with glacial acetic acid and concentrated. The residue was diluted with 30 ml of ether and washed with 10 ml of saturated NaHCO$_3$, 10 ml of H$_2$O, dried over anhydrous MgSO$_4$ and concentrated to give 230 mg of crude title enone. This was used without purification.

C.

[3α(Z),4β(1E,3S)]-7-[4-(3-Cyclohexyl-3-hydroxy-1-propenyl)tetrahydro-3-furanyl]-5-heptenoic acid, methyl ester and

D.

[3α(Z),4β(1E,3R)]-7-[4-(3-Cyclohexyl-3-hydroxy-1-propenyl)tetrahydro-3-furanyl]-5-heptenoic acid, methyl ester To 230 mg of title B enone (ca. 0.56 mmole) in 3 ml of methanol at 25° C. was added 132 mg of cerium trichloride (0.56 mmole, 1 eq.). After stirring at 25° C. for 10 minutes, the mixture was cooled to 0° C. To this mixture was added 20.5 mg of sodium borohydride (0.56 mmole, 4 eq.). This was stirred at 0° C. for 10 minutes, then poured into 100 ml of a saturated NH$_4$Cl solution, extracted with three 20 ml portions of ether, dried over anhydrous MgSO$_4$ and concentrated. Separation was done on an LPS-1 silica gel column, eluting with 20% EtOAc/hexanes to give 105 mg of the desired title C allylic alcohol as an oil.

EXAMPLE 14

[3α(Z),4β(1E,3S)]-7-[4-(3-Cyclohexyl-3-hydroxy-1-propenyl)tetrahydro-3-furanyl]-5-heptenoic acid To 95 mg of Example 13 methyl ester (0.27 mmole) in 8 ml of THF and 2 ml of H$_2$O at 0° C. was added dropwise 2.7 ml of a 1M lithium hydroxide solution (2.7 mmole, 10 eq.). The mixture was stirred at 25° C. for three hours and then concentrated. The residue was diluted with 5 ml of H$_2$O, acidified to pH 3 with a saturated oxalic acid solution and extracted with three 20 ml portions of ether. It was then dried over anhydrous MgSO$_4$ and concentrated. The residue was purified on a CC-7 silica gel column, eluting with a gradient of pentane/ether.

The product was kept under high vacuum for 7 days to give 65 mg of title acid as a clear oil.

TLC: Silica gel, 10% MeOH/CH$_2$Cl; R$_f$~0.4.
Anal Calcd for C$_{20}$H$_{32}$O$_4$: C, 71.39; H, 9.58; Found: C, 71.06; H, 9.70.

EXAMPLE 15

[3α(Z),4β(1E,3R)]-7-[4-(3-Cyclohexyl-3-hydroxy-1-propenyl)tetrahydro-3-furanyl]-5-heptenoic acid, methyl ester The title compound was prepared as described in Example 13, Part D.

EXAMPLE 16

[3α(Z),4β(1E,3R)]-7-[4-(3-Cyclohexyl-3-hydroxy-1-propenyl)tetrahydro-3-furanyl]-5-heptenoic acid To 54 mg of Example 15 ester (0.15 mmole) in 8 ml of THF and 2 ml of H$_2$O at 0° C. was added dropwise 1.5 ml of a 1N lithium hydroxide solution (1.5 mmole, 10 eq.). The mixture was stirred at 25° C. for 4 hours and then concentrated. The residue was diluted with 5 ml of H$_2$O, acidified to pH 3 with a saturated oxalic acid solution, extracted with three 20 ml portions of ether, dried over anhydrous MgSO$_4$ and concentrated. The residue was purified on a CC-7 silica gel column, eluting with a gradient of pentane/ether. The product was kept under high vacuum for 2 days to give 50 mg of title acid as an oil.

TLC: Silica gel; 10% MeOH/CH$_2$Cl$_2$1 R$_f$~0.4
Anal Calcd for C$_{20}$H$_{32}$O$_4$: C, 71.39; H, 9.58; Found: C, 71.16; H, 9.74.

EXAMPLE 17

[3α(Z),4β(1E,3S,4S)]-7-[Tetrahydro-4-(3-hydroxy-4-phenyl-1-pentenyl) -3-furanyl]-5-heptenoic acid, methyl ester

A.

[3α(Z),4β(1E)]-7-[Tetrahydro-4-(3-oxo-4-phenyl-1-pentenyl)-3-furanyl]-5-heptenoic acid, methyl ester To a solution of 166.6 mg of (+)-2-oxo-4-methyl-4-phenylmethyl dimethyl phosphonate (0.64 mmole, 1.1 eq.) in 5 ml of dry THF at −78° C. under an argon atmosphere was added dropwise a solution of 263.4 ml of a 2.5M solution of n-butyllithium in hexane (0.59 mm, 1.0 eq.). After stirring at −78° C. for 1 hour, the mixture was warmed to 25° C. and a solution of 140 mg of Example 13, Part A aldehyde (0.59 mmole) in 5 ml of dry THF was added. After stirring at 25° C. for 2 hours, the reaction was quenched with glacial acetic acid and concentrated. The residue was diluted with 50 ml of ether and washed with 20 ml of saturated NaHCO$_3$, 20 5 ml of H$_2$O, dried over anhydrous MgSO$_4$ and concentrated.

The residue was purified on a silica gel column, eluting with 20% EtOAc/hexanes to give 117 mg of title enone as an oil.

B.

[3α(Z),4β(1E,3S,4S)]-7-[Tetrahydro-4-(3-hydroxy-4-phenyl-1-pentenyl)-3-furanyl]-5-heptenoic acid, methyl ester and

C.

[3α(Z),4β(1E,3R,4S)]-7-[Tetrahydro-4-(3-hydroxy-4-phenyl-1-pentenyl)-3-furanyl]-5-heptenoic acid, methyl ester To 117 mg of title A enone (0.31 mmole) in 5 ml of methanol at 25° C. was added 77 mg of cerium trichloride (0.31 mmole, 1 eq.). After stirring at 25° C. for 10 minutes the mixture was cooled to 0° C., 12 mg of sodium borohydride (0.31 mmole, 4 eq.) was added and the mixture was stirred at 0° C. for 15 minutes. The reaction mixture was then poured into 50 ml of a saturated NH$_4$Cl solution and extracted with three 20 ml portions of ether. The combined ethereal extract was dried over anhydrous MgSO$_4$ and concentrated to give 107 mg of a mixture.

Separation was done on a silica gel column, eluting with 25% EtOAc/hexane to give 50 mg of title C ester and 25 mg of title B ester.

TLC of C: Silica gel; EtOAc/hexane (1:1); R$_f$~0.5
TLC of B: Silica gel; EtOAc/hexane (1:1); R$_f$~0.4

EXAMPLE 18

[3α(Z),4β(1E,3S,4S)]-7-[Tetrahydro-4-(3-hydroxy-4-phenyl-1-pentenyl)-3-furanyl]-5-heptenoic acid To 25 mg of Example 17 ester (0.07 mmole) in 2.8 ml of THF at 25° C. was added 0.7 ml of a 1M lithium hydroxide solution (0.7 mmole, 10 eq.). The mixture was stirred at 25° C. for 20 hours, and then concentrated. The residue was diluted with 5 ml of H$_2$O, acidified to pH 3 with a saturated oxalic acid solution and extracted with three 10 ml portions of ether. The combined ethereal extract was washed with two 10 ml portions of H$_2$O, dried over anhydrous MgSO$_4$ and concentrated. The product was kept under high vacuum for 2 days to yield 20 mg of title acid as an oil.

TLC: Silica gel; 10% MeOH/CH$_2$Cl$_2$; R$_f$~0.4

Anal Calcd for C, 73.71; H, 8.43; Found: C, 73.91; H, 8.62.

EXAMPLE 19

[3α(Z),4β(1E,3R,4S)]-7-[Tetrahydro-4-(3-hydroxy-4-phenyl-1-pentenyl)-3-furanyl]-5-heptenoic acid To 60 mg of Example 17 Part C methyl ester (0.16 mmole) in 4 ml of THF and 1 ml of H$_2$O at 0° C. was added dropwise 1.6 ml of a 1M lithium hydroxide solution (1.6 mmole, 10 eq.). The mixture was stirred at 25° C. for 6 hours and then concentrated. The residue was diluted with 5 ml of H$_2$O and acidified to pH 3 with a saturated oxalic acid solution, extracted with three 20 ml portions of ether, dried over anhydrous MgSO$_4$ and concentrated. The residue was purified on a CC-7 silica gel column, eluting with a gradient of pentane/ether.

The product was kept under high vacuum for 2 days to give 26 mg of title acid as an oil.

TLC: silica gel; 10% MeOH/CH$_2$Cl$_2$; R$_f$~0.5

Anal Calcd for C$_{22}$H$_{30}$O$_4$, 0.2 mole H$_2$O: C, 73.01 H, 8.46; Found: C, 73.01; H, 8.51.

EXAMPLE 20

[3α(Z),4α(1E,3S)]-7-[Tetrahydro-4-(3-hydroxy-1-octenyl)-3-furanyl]-2,5-heptadienoic acid

A.

[3α(Z),4α(1E,3S)]-7-[Tetrahydro-4-(3-tetrahydropyranoxy-1-octenyl)-3-furanyl]-5-heptenoic acid, methyl ester To a solution of 2.37 g of [3α(Z),4β(1E,3S)]-7-[tetrahydro-4-(3-hydroxy-1-octenyl)-3-furanyl]-5-heptenoic acid, methyl ester (prepared as described in Example 1) (7.0 mmole) in 20 ml of dry methylene chloride is added with stirring a catalytic amount of p-toluene sulfonic acid, followed by 720 μl of dihydropyran (DHP) (8.0 mmole) at 0°-5° C. The reaction mixture is stirred at 0°-5° C. for 40 minutes, whereupon it is washed with aqueous sodium bicarbonate solution. The methylene chloride layer is separated and the aqueous layer is extracted with ether. The combined organic extract is dried over anhydrous magnesium sulfate and concentrated under reduced pressure. Purification by flash chromatography on a silica gel column gives 2.75 g of desired title THP-ether (eluting solvent 10-15% ethylacetate in hexane).

B.

[3α(Z),4α(1E,3S)]-7-[Tetrahydro-4-(3-tetrahydropyranoxy-1-octenyl)-3-furanyl]-2-selenophenyl-5-heptenoic acid, methyl ester To a solution of 2 ml of distilled diisopropylamine (13 mmole, distilled over CaH$_2$) in 30 ml of dry THF, cooled at −78° C. in a dry ice-acetone bath is added dropwise 7.5 ml of a 1.6 M solution of n-butyllithium in hexane (12 mmole). The solution of lithium diisopropylamide so formed is stirred at −78° C. for 30 minutes, whereupon a solution of 2.53 g of Part A THP-ether (6 mmole) in 15 ml of dry THF is added dropwise over a period of 10 minutes. The colorless solution is stirred at −78° C. for an additional 30 minutes, whereupon a solution of 3.75 g of diphenyl-diselenide (12 mmole) in 5 ml of dry THF is added dropwise. Initially the yellow color of diselenide discharges immediately upon addition. The yellow solution is stirred at −78° C. for 30 minutes, whereupon the cooling bath is removed. After 30 minutes, the reaction mixture is quenched by addition of aqueous ammonium chloride solution. It is then diluted with water and the organic layer is separated. The aqueous layer is extracted with ether. The combined organic extract is dried over anhydrous magnesium-sulfate and concentrated under reduced pressure. The crude residue is chromatographed on a silica gel column. Elution with 5-15% ethyl acetate in hexane gives 2.89 g of title α-selenophenyl ester as a colorless oil.

C.

[3α(Z),4α(1E,3S)]-7-[Tetrahydro-4-(3-tetrahydropyranoxy-1-octenyl)-3-furanyl]-2-selenophenyl-5-heptenoic acid To a solution of 1.36 g of Part B seleno-ester (~2 mmole) in 12 ml of distilled THF and 3 ml of water is added with stirring 9 ml of a 1N aqueous lithium hydroxide solution. The heterogeneous reaction mixture is stirred at room temperature under an argon atmosphere for 2 days, whereupon it is acidified by careful addition of 2N aqueous hydrochloric acid solution. Extraction with ether (X3), drying of the ether extract over anhydrous magnesium sulfate and finally concentration under reduced pressure gives 1.3 g of desired title acid as a colorless oil.

D.

[3α(Z),4α(1E,3S)]-7-[Tetrahydro-4-(3-tetrahydropyranoxy-1-octenyl)-3-furanyl]-2,5-heptadienoic acid A solution of 423 mg of Part C α-selenophenyl acid (0.73 mmole) in 10 ml of distilled THF is treated with 500 μl of a 30% aqueous hydrogen peroxide solution at 0°-5° C. After a few minutes, the cooling bath is removed and the reaction mixture is stirred at room temperature for 1 hour. It is then diluted with ether and washed several times with water. The organic extract is dried over anhydrous magnesium sulfate and concentrated under reduced pressure. The crude oil is chromatographed on a CC-7 silica gel column and eluted with 20-50% ethyl acetate in hexane to obtain 245 mg of title acid.

E.
[3α(Z),4α(1E,3S)]-7-[Tetrahydro-4-(3-hydroxy-1-octenyl)-3-furanyl]-2,5-heptadienoic acid A solution of 245 mg of Part D α,β-unsaturated acid in 10 ml of dimethoxy ethane and 3 ml of 2N HCl is stirred at room temperature for 8 hours. The reaction mixture is diluted with ether and washed thoroughly with water. The aqueous layer is re-extracted with ether twice. The combined organic extract is dried over anhydrous magnesium sulfate and concentrated under reduced pressure. The crude residue is chromatographed on a CC-7 silica gel column and eluted with 20–50% ethyl acetate in hexane to obtain 185 mg of title 2,3-dehydro acid.

EXAMPLE 21

[3α(Z),4α(1E,3S)]-7-[Tetrahydro-4-(3-hydroxyoctenyl)-3-furanyl]heptanoic acid

A.
(3α,4α)-7-[Tetrahydro-4-(1-hydroxy-1-hydroxymethylmethyl)-3-furanyl]heptanoic acid, methyl ester A mixture of 500 mg of Example 1 Part O diol, 100 mg of a 10% palladium over carbon in 80 ml of EtOAc and 4 ml of glacial acetic acid is shaken in a Parr bottle under 50 lb. of hydrogen pressure at 25° C. for 24 hours. The mixture is then filtered through a bed of Celite. The filtrate is concentrated to give title A diol.

B. (3α,4α)-7-[Tetrahydro-4-formyl-3-furanyl]heptanoic acid, methyl ester

To a solution of 272 mg of title A diol (1 mmole) in 5 ml methanol at 25° C. is added a solution of 230 mg of sodium m-periodate in 1 ml H$_2$O. The mixture is stirred at 25° C. for 30 minutes, then extracted with 3–10 ml portions of CH$_2$Cl$_2$. The organic layer is dried over anhydrous MgSO$_4$ and concentrated to give title aldehyde.

C.
[3α,4α(1E,3S)]-7-[Tetrahydro-4-(3-hydroxy-1-octenyl)-3-furanyl]heptanoic acid Following the procedure of Example 1 Parts Q and R and Example 2 except substituting the above Part B aldehyde for the Example 1 Part P aldehyde, the title acid is obtained.

EXAMPLE 22

[3α(Z),4α(1E,3S)]-7-[Tetrahydro-4-(3-hydroxy-3-phenyl-1-propenyl)-3-furanyl]-5-heptenoic acid Following the procedure of Examples 1 and 2 except substituting 2-oxo-2-phenyl ethyldimethylphosphonate for 2-oxo-heptyldimethylphosphonate, the title compound is obtained.

EXAMPLE 23

[3α(Z),4α(1E,3S)]-7-[Tetrahydro-4-(3-hydroxy-4-phenyl-1-butenyl)-3-furanyl]-5-heptenoic acid Following the procedure of Examples 1 and 2 except substituting 2-oxo-3-phenyl propyldimethylphosphonate for 2-oxo-heptyldimethylphosphonate, the title compound is obtained.

EXAMPLE 24

[3α(Z),4α(1E,3S)]-7-[Tetrahydro-4-(3-hydroxy-4-cyclohexyl-1-butenyl)-3-furanyl]-5-heptenoic acid Following the procedure of Examples 1 and 2 except substituting 2-oxo-3-cyclohexyl propyldimethylphosphonate for 2-oxo-heptyldimethylphosphonate, the title compound is obtained.

EXAMPLE 25

[3α(Z),4α(1E,3S)]-7-[Tetrahydro-4-(3-hydroxy-2-ethoxy-1-propenyl)-3-furanyl]-5-heptenoic acid Following the procedure of Examples 1 and 2 except substituting 2-oxo-2-ethoxy ethyldimethylphosphonate for 2-oxo-heptyldimethylphosphonate, the title compound is obtained.

EXAMPLE 26

[3α(Z),4α(1E,3S)]-7-[4-(3-Cyclohexyl-3-hydroxy-1-propenyl)tetrahydro-3-furanyl]-2,5-heptadienoic acid Following the procedure of Example 20 except substituting the Example 5 compound for the Example 1 compound in Part A, the title compound is obtained.

EXAMPLE 27

[3α(Z),4α(1E,3S)]-7-[Tetrahydro-4-(3-hydroxy-4-phenyl-1-pentenyl)-3-furanyl]-2,5-heptadienoic acid Following the procedure of Example 20 except substituting the Example 11 compound for the Example 1 compound in Part A, the title compound is obtained.

EXAMPLE 28

[3α(Z),4α(1E,3S)]-7-[Tetrahydro-4-(3-hydroxy-2-ethoxy-1-propenyl)-3-furanyl]-5-heptenoic acid Following the procedure of Examples 1 and 2 except substituting the Example 25 compound for the Example 1 compound in Part A, the title compound is obtained.

EXAMPLE 29

[3α(Z),4α(1E,3S)]-7-[4-(3-Cyclohexyl-3-hydroxy-1-propenyl)tetrahydro-3-furanyl]heptanoic acid Following the procedure of Example 21 and Examples 5 and 6 except substituting the Example 21 Part B aldehyde for the Example 1 Part P aldehyde used in Example 5 Part A, the title compound is obtained.

EXAMPLE 30

[3α(Z),4α(1E,3S)]-7-[Tetrahydro-4-(3-hydroxy-4,4-dimethyl-1-octenyl)-3-furanyl]heptanoic acid Following the procedure of Example 21 and Examples 7 and 8 except substituting the Example 21 Part B aldehyde for the Example 1, part P aldehyde used in Example 7 Part A, the title compound is obtained.

EXAMPLE 31

[3α(Z),4α(1E,3S)]-7-[Tetrahydro-4-(3-hydroxy-4-phenyl-1-pentenyl)-3-furanyl]heptanoic acid Following the procedure of Example 21 and Examples 11 and 12 except substituting the Example 21 Part B aldehyde for the Example 1 Part P aldehyde used in Example 11 Part A, the title compound is obtained.

EXAMPLE 32

[3α(Z),4β(1E,3S)]-7-[4-(3-Cyclohexyl-3-hydroxy-1-propenyl)Tetrahydro-3-furanyl]heptanoic acid Following the procedure of Example 21 and Examples 13 and 14 except substituting the Example 21 Part B aldehyde for the Example 1 Part P aldehyde used in Example 13 Part A, the title compound is obtained.

EXAMPLE 33

[3α(Z),4α(1E,3S)]-7-[Tetrahydro-4-(3-hydroxy-1-octyl)-3-furanyl-5-heptenoic acid, methyl ester

A.
[3α(Z),4α(1E,3S)]-7-[Tetrahydro-4-(3-oxo-1-octyl)-3-furanyl]-5-heptenoic acid, methyl ester To a suspension of 686 mg of purified cuprous bromide (4.8 mmole) in 12 ml of dry THF, cooled at 0°–5° C. is added with stirring 1.35 ml of a 3.5M solution of red-Al (sodium bis(2-methoxyethoxy)aluminum hydride) in toluene dropwise. The solution is stirred at 0°–5° C. for 30 minutes, whereupon it is cooled to −78° C. and 2 ml of n-butanol (18 mmole) is added rapidly, followed by a solution of 672 mg of Example 1 Part Q enone (2 mmole) in 4 ml of dry THF. After 10 minutes at −78° C., the reaction mixture is warmed to −20° C. and left for an additional 1 hour. The reaction mixture is quenched by addition of 70 ml of water and then poured into saturated ammonium chloride solution and extracted with ether (X3). The ether extract is dried over anhydrous magnesium sulfate, filtered and the filtrate is concentrated under reduced pressure. 675 Mg of desired title ketone is obtained.

B.
[3α(Z),4α(1E,3S)]-7-[Tetrahydro-4-(3-hydroxy-1-octyl)-3-furanyl]-5-heptenoic acid, methyl ester To a solution of 338 mg of Part A ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 38 mg of solid sodium borohydride (∼1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous hydrochloric acid solution. The ether extract is dried over anhydrous MgSO₄ and concentrated under reduced pressure. The crude residue is chromatographed on a silica gel column and eluted with 30–50% ethyl acetate in hexane to obtain the desired 3S-alcohol.

EXAMPLE 34

[3α(Z),4α(1E,3S)]-7-[Tetrahydro-4-(3-hydroxy-1-octyl)-3-furanyl]-5-heptenoic acid Following the procedure of Example 2 except substituting the Example 33 methyl ester for the Example 1 methyl ester, the title compound is obtained.

EXAMPLE 35

[3α(Z),4α(1E,3S)]-7-[4-(3-Cyclohexyl-3-hydroxy-1-propyl)tetrahydro-3-furanyl]-5-heptenoic acid, methyl ester and free acid Following the procedure of Examples 33 and 34 except substituting the Example 5 Part A ketone for the Example 1 Part Q ketone, the title compound is obtained.

EXAMPLE 36

[3α(Z),4α(1E,3S)]-7-[Tetrahydro-4-(3-hydroxy-4,4-dimethyl-1-octyl)-3-furanyl]-5-heptenoic acid, methyl ester and free acid Following the procedure of Examples 33 and 34 except substituting the Example 7 Part A ketone for the Example 1 Part Q ketone, the title compound is obtained.

EXAMPLE 37

[3α(Z),4α(1E,3S,4S)]-7-[Tetrahydro-4-(3-hydroxy-4-phenyl-1-pentyl)-3-furanyl]-5-heptenoic acid, methyl ester and free acid Following the procedure of Examples 33 and 34 except substituting the Example 11 Part A ketone for the Example 1 Part Q ketone, the title compound is obtained.

EXAMPLE 38

[3α(Z),4β(1E,3S)]-7-[4-(3-Cyclohexyl-3-hydroxy-1-propyl)tetrahydro-3-furanyl]-5-heptenoic acid, methyl ester and free acid Following the procedure of Examples 33 and 34 except substituting the Example 13 Part A ketone for the Example 1 Part Q ketone, the title compound is obtained.

EXAMPLES 39 TO 48

It will be appreciated that following the procedure as described in the specification and in the working Examples as outlined above, any of the following compounds may be prepared $$\begin{array}{c} \diagup CH_2-A-(CH_2)_m-B-COOH \\ O \\ \diagdown Q-CH-R^1 \\ | \\ OH \end{array}$$

| Ex. No. | A | m | B | Q | R¹ |
|---|---|---|---|---|---|
| 39 | CH=CH | 4 | — | CH=CH | C₄H₉ |
| 40 | CH=CH | 5 | CH=CH | CH=CH | C₆H₅ |
| 41 | CH—CH₂<br>\|<br>CH₃ | 6 | CH=CH | (CH₂)₂ |  |
| 42 | — | 7 | CH=CH | (CH₂)₂ | C₆H₅CH₂ |
| 43 | (CH₂)₂ | 6 | — | (CH₂)₂ | C₅H₁₁ |
| 44 | (CH₂)₂ | 8 | — | CH=CH | C₃H₇O |
| 45 | (CH₂)₂ | 3 | — | (CH₂)₂ | C₆H₅(CH₂)₂ |
| 46 | CH=CH | 2 | — | CH=CH | C₂H₅O |
| 47 | CH=CH | 1 | CH=CH | (CH₂)₂ |  |

-continued

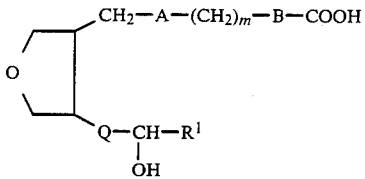

| Ex. No. | A | m | B | Q | R¹ |
|---|---|---|---|---|---|
| 48 | CH=CH | 3 | — | CH=CH | CH₃O |

EXAMPLE 49

[3α(Z),4α(1E,3S)]-7-[4-(3-Cyclohexyl-3-hydroxy-1-propyl)tetrahydro)-3-furanyl]-2,5-heptadienoic acid Following the procedure of Example 20 except substituting the Example 35 methyl ester for the Example 1 methyl ester, the title compound is obtained.

EXAMPLE 50

[3α(Z),4α(1E,3S)]-7-[Tetrahydro-4-(3-hydroxy-1-octyl)-3-furanyl]-2,5-heptadienoic acid Following the procedure of Example 20 except substituting the Example 33 methyl ester for the Example 1 methyl ester, the title compound is obtained.

EXAMPLE 51

[3α(Z),4α(1E,3S)]-7-[Tetrahydro-4-(3-hydroxy-4,4-dimethyl-1-octyl)-3-furanyl]-2,5-heptadienoic acid Following the procedure of Example 20 except substituting the Example 36 methyl ester for the Example 1 methyl ester, the title compound is obtained.

EXAMPLE 52

[3α(Z),4α(1E,3S)]-7-[Tetrahydro-4-(3-hydroxy-4-phenyl-1-pentyl)-3-furanyl]-2,5-heptadienoic acid Following the procedure of Example 20 except substituting the Example 37 methyl ester for the Example 1 methyl ester, the title compound is obtained.

EXAMPLE 53

[3α(Z),4α(1E,3S)]-7-[4-(3-Cyclohexyl-3-hydroxy-1-propyl)-3-furanyl]-2,5-heptadienoic acid Following the procedure of Example 20 except substituting the Example 38 methyl ester for the Example 1 methyl ester, the title compound is obtained.

What is claimed is:

1. A compound of the structure

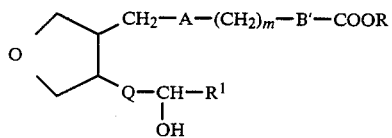

including all stereoisomers thereof, wherein A is —(CH₂)₂, —CH=CH— or a single bond; m is 1 to 8; B' is —CH=CH— or a single bond, but where B' is —CH=CH—, m is 1 to 6; Q is —CH=CH— or —(CH₂)$_n$—; n is 1 to 4; R is H, lower alkyl or alkali metal; and R¹ is aryl, cycloalkyl or cycloalkylalkyl.

2. The compound as defined in claim 1 wherein said compound is the cis isomer.

3. The compound as defined in claim 1 wherein said compound is the trans isomer.

4. The compound as defined in claim 1 wherein A is —CH=CH—.

5. The compound as defined in claim 1 wherein R is H.

6. The compound as defined in claim 1 wherein m is 2 to 5 and B' is a single bond.

7. The compound as defined in claim 1 wherein Q is —CH=CH—.

8. The compound as defined in claim 1 wherein R¹ is phenyl or cycloalkyl, including all isomers thereof.

9. The compound as defined in claim 1 having the name [3α(Z),4α(1E,3S)]-7-[4-(3-cyclohexyl-3-hydroxy-1-propenyl)tetrahydro-3-furanyl]-5-heptenoic acid or the methyl ester thereof, including all stereoisomers thereof.

10. The compound as defined in claim 1 having the name [3α(Z),4β(1E,3S)]-7-[4-(3-cyclohexyl-3-hydroxy-1-propenyl)tetrahydro-3-furanyl]-5-heptenoic acid or the methyl ester thereof, including all stereoisomers thereof.

11. The compound as defined in claim 1 having the name [3α(Z),4β(1E,3R)]-7-[4-(3-cyclohexyl-3-hydroxy-1-propenyl)tetrahydro-3-furanyl]-5-heptenoic acid or the methyl ester thereof, including all stereoisomers thereof.

12. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

13. The method as defined in claim 12 wherein said compound is administered in an amount within the range of from about 1 to about 100 mg/kg.

14. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

15. A method of inhibiting platelet aggregation which comprises administering to a mammalian host an effective amount of a compound as defined in claim 1 or a pharmaceutically acceptable salt thereof.

16. A method of inhibiting bronchoconstriction associated with asthma, which comprises administering to a mammalian host an effective amount of a compound as defined in claim 1 or a pharmaceutically acceptable salt thereof.

17. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,542,155

DATED : September 17, 1985

INVENTOR(S) : Jagabandhu Das

It is certified that error appears in the above-identified patent and that said Letters Patent is hereby corrected as shown below:

Column 7, line 47, structure IV should read

-- 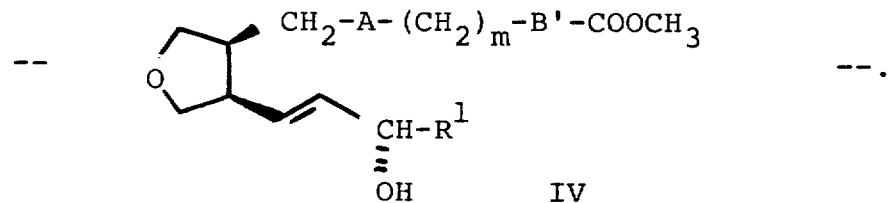 --.

Column 11, line 61, structure IA should read

-- 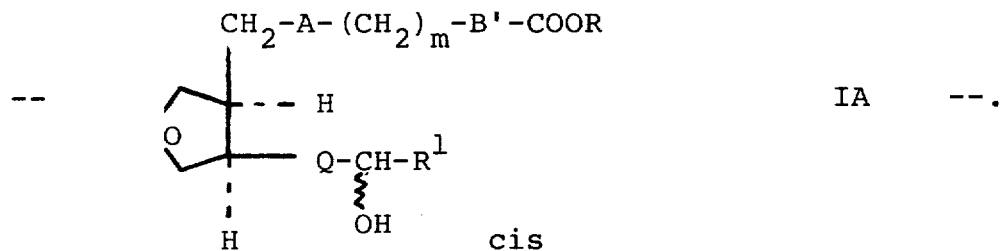 IA --.

Column 12, line 1, structure IB should read

-- 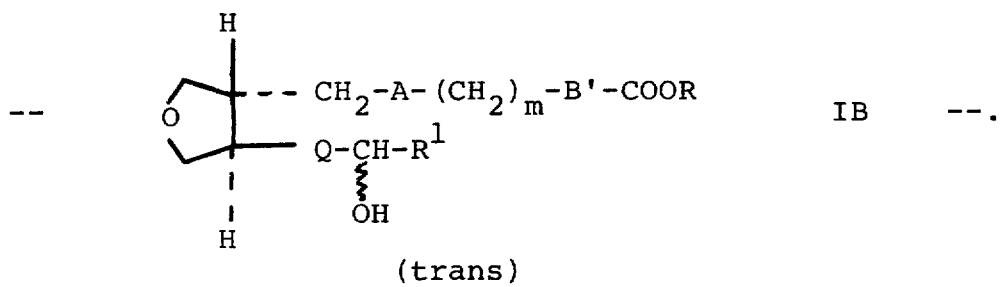 IB --.

UNITED STATES PATENT AND TRADEMARK OFFICE
CERTIFICATE OF CORRECTION

PATENT NO. : 4,542,155

DATED : September 17, 1985

INVENTOR(S) : Jagabandhu Das

It is certified that error appears in the above-identified patent and that said Letters Patent is hereby corrected as shown below:

Column 12, line 12, "R(⊕)" should read --R($\beta$)--.
Column 12, line 14 "arachidonicinduced" should read --arachidonic-induced--.
Column 23, line 52, "4$\beta$" should read --4$\alpha$--.

Signed and Sealed this

Ninth Day of December, 1986

Attest:

DONALD J. QUIGG

*Attesting Officer*     *Commissioner of Patents and Trademarks*